United States Patent
Drzewiecki et al.

[11] Patent Number: 5,605,156
[45] Date of Patent: Feb. 25, 1997

[54] FLEXIBLE DIAPHRAGM TONOMETER

[75] Inventors: Gary M. Drzewiecki, Princeton, N.J.;
Robert D. Butterfield, Poway, Calif.

[73] Assignee: Rutgers University, Pizcataway, N.J.

[21] Appl. No.: 442,033

[22] Filed: May 16, 1995

Related U.S. Application Data

[62] Division of Ser. No. 154,801, Nov. 17, 1993, Pat. No. 5,439,001.

[51] Int. Cl.$^6$ ................................................. A61B 5/021
[52] U.S. Cl. ........................... 128/672; 128/687; 128/690; 128/748
[58] Field of Search ..................................... 128/672, 673, 128/687–690, 748, 675; 73/223

[56] References Cited

U.S. PATENT DOCUMENTS

| | | | |
|---|---|---|---|
| 4,561,447 | 12/1985 | Kawamura et al. | 128/687 |
| 4,610,256 | 9/1986 | Wallace | 128/675 |
| 4,869,261 | 10/1989 | Penez | 128/667 |
| 4,920,972 | 5/1990 | Frank et al. | 128/675 |
| 4,928,700 | 5/1990 | Herada | 128/672 |
| 4,928,702 | 5/1990 | Cousin | 128/678 |
| 5,000,049 | 3/1991 | Cooper et al. | 128/748 |
| 5,119,822 | 6/1992 | Niwa | 128/672 |
| 5,154,680 | 10/1992 | Drzewiecki et al. | 128/672 |
| 5,158,091 | 10/1992 | Butterfield et al. | 128/672 |
| 5,195,522 | 3/1993 | Pytel et al. | 128/680 |
| 5,450,852 | 9/1995 | Archibald et al. | 128/687 |

*Primary Examiner*—Angela D. Sykes
*Assistant Examiner*—Robert L. Nasser, Jr.
*Attorney, Agent, or Firm*—Fulwider Patton Lee & Utecht, LLP

[57] ABSTRACT

A pressure waveform monitor for non-invasively monitoring the pressure waveform inside a vessel, such as an artery, includes a flexible diaphragm extended across an opening of a container containing a fluid. The flexible diaphragm is placed against tissue surrounding an artery such that arterial pressure causes a deflection in the diaphragm. A deflection in the diaphragm causes the fluid to be redistributed throughout the container which is effectively divided into an array of volume compartments. The relative volume distribution is determined through impedance plethysmography. The diaphragm is maintained in a calibrated position by maintaining the array of volume compartments at relatively unchanged volumes. When the relative volumes remain essentially unchanged, calibrated tonometry is possible. The pressure within the container is then used to determine the pulse waveform and the pressure within the artery.

14 Claims, 9 Drawing Sheets

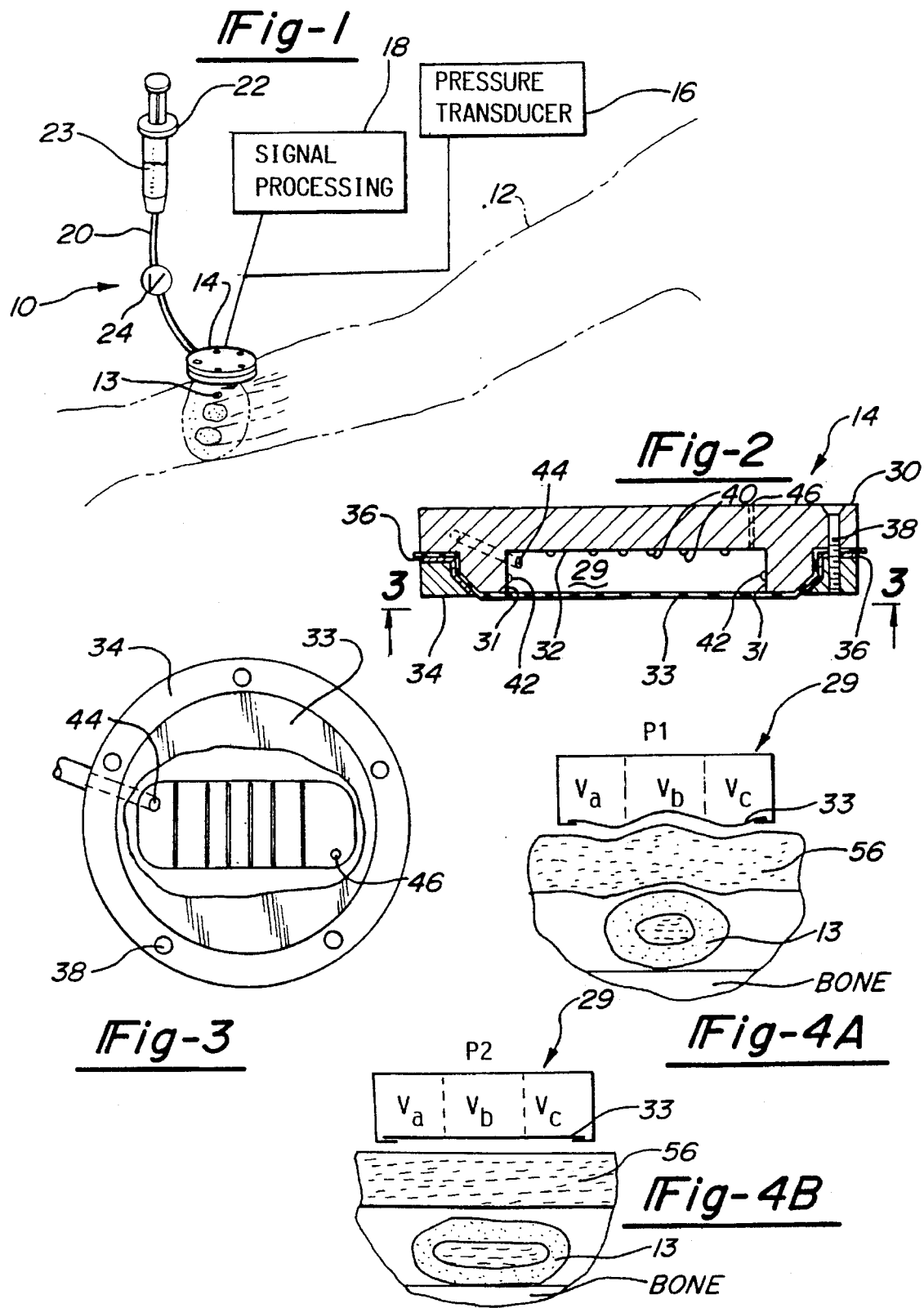

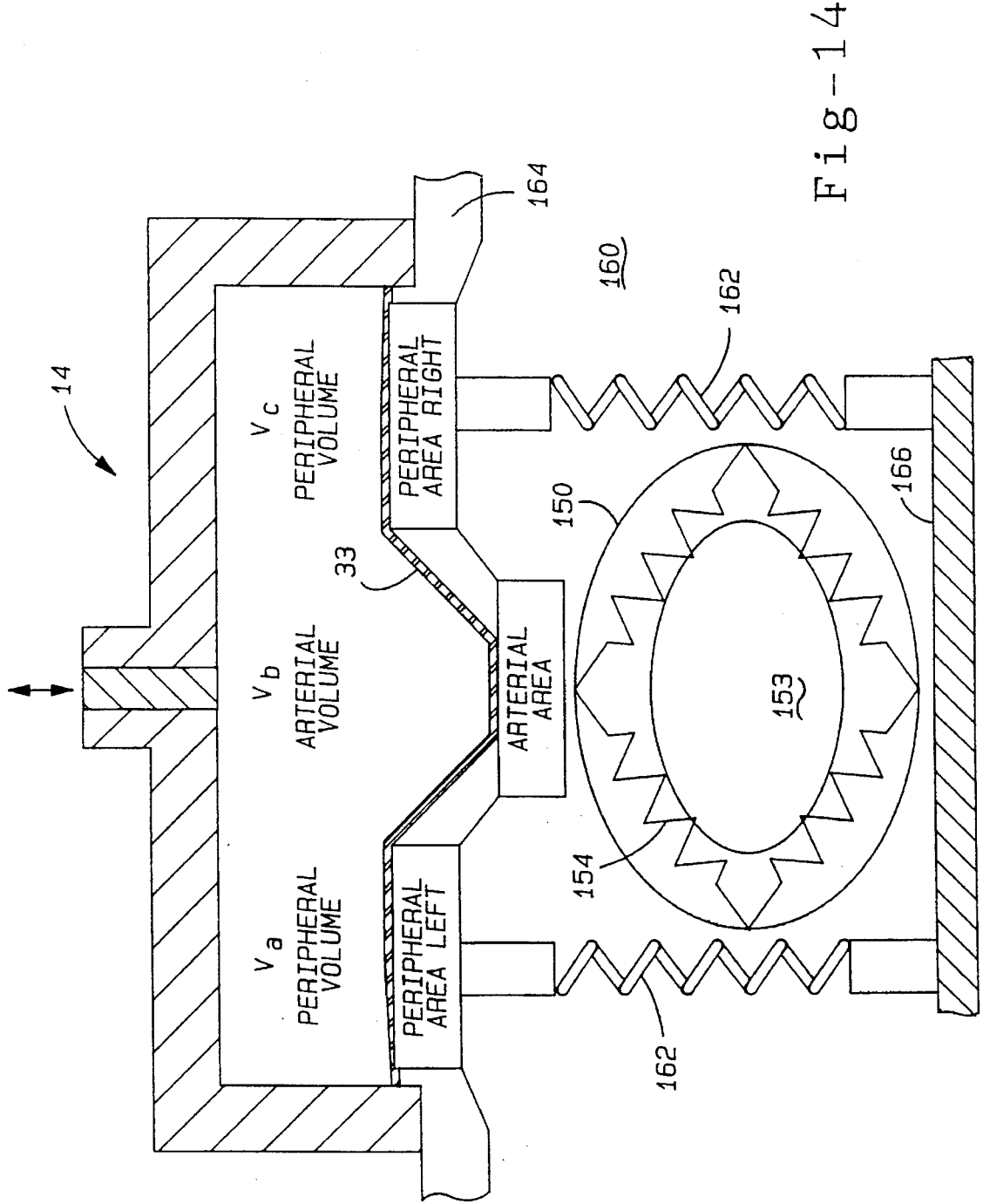

5,605,156

FLEXIBLE DIAPHRAGM TONOMETER

This application is a Divisional Application of U.S. application Ser. No. 154,801, filed on Nov. 17,1993, now U.S. Pat. No. 5,439,001.

BACKGROUND OF THE INVENTION

This invention relates generally to a system for monitoring waveforms, and more specifically, to a device and method for non-invasively monitoring the blood pressure waveform in a blood vessel by detecting the pressure within a fluid filled container having one wall formed of a flexible diaphragm that is placed over the tissue covering the blood vessel when the device is maintained in a calibrated condition.

TECHNICAL FIELD

Methods for accurately monitoring the blood pressure waveform have been under investigation for some time. While invasive methods can provide accurate waveforms, the trauma caused to the patient makes the technique undesirable in many cases. One such method involves the use of a fluid filled catheter inserted into a patient's artery. While accurate blood pressure measurements can be obtained by this method, the negative effects on the patient, may, in many cases, outweigh the benefits of achieving accurate results from such a method.

Routine methods of monitoring a patient's blood pressure waveform include the widely used auscultatory method known as the Korotkoff method. This method is non-invasive, however, it only provides a measurement of systolic and diastolic pressure on an intermittent basis; it does not provide the entire waveform on a continuous basis. Furthermore, use of this method often yields inaccurate results. Moreover, the rate at which blood pressure can be recorded is limited by the inflation and deflation rate of the occlusive cuff. Therefore, true beat-to-beat continuous blood pressure monitoring is not possible using this method.

While the occlusive cuff instruments have been adequate for ascertaining long term trends in patient blood pressure, short term variation has previously not been easily measured non-invasively. Techniques that offer potential in this area include a method using a pressure-feedback technique that records the blood pressure in a patient's finger. Feedback error signals are obtained using optical plethysmography. Alternatively, arterial tonometry methods include determining arterial blood pressure from a superficial pulse artery, such as the radial artery, by relating contact stress or forces at the surface of the skin to blood pressure. Such methods include several drawbacks. One Is that blood pressure measurement is too peripheral and undesirably influenced by the smooth muscle tone of the resistance arteries. Secondly, it is difficult to implement arterial tonometry with previously available devices because a high degree of miniaturization is required for contact stress sensors used in such devices.

For example, one type of arterial tonometer includes an array of individual transducer elements placed directly on the patient's tissue overlying an artery or blood vessel from which blood pressure is to be determined. The elements directly sense the mechanical forces in the tissue with which each of them is in contact. The elements of the array are dimensioned and spaced apart from each other such that a plurality of these elements are required to cover the entire diameter or width of the underlying blood vessel; the size of each element is designed to cover only a small fraction of the diameter of the underlying blood vessel. The pressure of the array against the tissue is increased to properly applanate the underlying vessel without causing occlusion. The fluid pressure within the artery is then conducted through the vessel wall and the overlying tissue to the transducers.

A significant drawback to such devices includes the use of the discrete elements. It has been found that with such tonometers a continuous contour of the tissue stresses under the array is not obtained. Additionally, it is believed that in prior methods no compensation means is provided for motion artifacts which may affect the forces translated to the sensors from the artery.

In view of the above, there is a need for true beat-to-beat, continuous arterial blood pressure measurement. Current research indicates that changes in the pulse waveform due to wave reflection can be responsible for an increase in systolic pressure. Monitoring such a pulse waveform can be crucial, for example, during surgery. Cuff-based techniques are used to monitor blood pressure during surgery. However, a cuff-based technique provides limited ability to monitor the pulse waveform continuously. Similarly, continuous measurement of pressure during exercise has been limited.

Therefore, it is desirable to provide an arterial tonometer designed for the continuous measurement of blood pressure. Such a tonometer preferably eliminates the need for high resolution sensor technology and has the ability to monitor the pressure within vessels smaller than the radial artery. This invention addresses these needs and provides the additional capability of measuring the mechanical compliance of the vessel being monitored.

SUMMARY OF THE INVENTION

This invention generally provides a pressure waveform monitor for non-invasively monitoring the pressure waveform inside a vessel, such as an artery. A device in accordance with this invention includes a container for holding fluid. The container preferably has three rigid side walls with an opening between two of the walls. A flexible diaphragm is preferably extended across the opening such that the container is effectively closed by the diaphragm. The diaphragm is capable of conforming to the contours of the human body and is adaptable to bending responsively to vessel pressure when the diaphragm is properly placed adjacent such a vessel. Means for dividing the container into adjacent, equal compartments are provided. The compartments are in relative communication such that the fluid within the container moves freely between the compartments. The device also includes means for determining the relative volumes of the compartments when the diaphragm bends responsively to vessel pressure and thereby distributes the fluid throughout the container. Further, means for supplying additional fluid to the container when the relative volumes of the compartments are changing is provided such that the relative volumes of the various compartments can be maintained relatively unchanged to thereby maintain the diaphragm in a calibrated, rest position. Lastly, means for determining the pressure within the container are provided for monitoring the vessel pressure waveform when the relative volumes of the compartments of the container are relatively unchanged and the diaphragm is therefore effectively maintained in its calibrated rest position.

In a preferred embodiment, the container sidewalls are formed from a lightweight plexiglass. The container is preferably a rectangular channel sealed off by the diaphragm. The diaphragm is preferably formed of a sheet of polyurethane having an approximate thickness of 4 mils (4/1000 inch).

The container is preferably divided into compartments which serve as an array of volume transducers. A means for measuring volume is provided which could include a microwave sensor, an ultrasound sensor or optics adapted to detecting volume, for example. The relative volumes of these transducers can also be detected by a variety of techniques commonly referred to as plethysmography. Preferably, impedance plethysmography is implemented because the volume compartments are filled with fluid providing a constant resistivity. In the presently preferred embodiment a saline solution is used because of its conductive properties. Alternative fluids include other conductive liquids, gases or gels. Whatever conductive medium or fluid is chosen will have a different resistivity. The electrical resistance of each compartment or volume transducer can then be related to the relative volume of each compartment.

The container is preferably divided into an array of volume transducers using volume measuring electrodes placed at equal spacing along a container wall that is parallel to and opposite the diaphragm. In this manner, a pair of electrodes defines a volume compartment and the volume of the compartment is calibrated by measuring the electrical resistance of the compartment. Two stainless steel electrodes are preferably placed at each end of the container on the two sidewalls that are perpendicular to the diaphragm. The latter two electrodes provide the ability to inject a current through the fluid such that a voltage can be measured across each pair of volume electrodes to determine the individual volume within each volume compartment. The resistance of each volume compartment varies inversely with the measured volume.

In one embodiment, the means for supplying additional noncompressible fluid to the container includes a reservoir filled with saline and a catheter appropriately connected to a fluid inlet defined in one of the rigid sidewalls of the container. When the relative volumes of the array of volume compartments are changing undesirably, additional saline fluid is supplied to the container from the reservoir. When the volumes of the respective volume compartments have relatively unchanged volumes due to arterial pulsations, the diaphragm is maintained in a calibrated, rest position. The pressure within the container when the diaphragm is maintained in the rest position allows a user to determine the pressure waveform within the blood vessel through the use of suitable electronics.

The method associated with the present invention for non-invasively monitoring the pressure waveform of a vessel, such as an artery, includes four basic steps. First, one provides the container filled with the noncompressible fluid having the flexible diaphragm as one side of the container. Second, the flexible diaphragm is pressed against tissue covering the vessel of interest thereby deforming the diaphragm across a portion of the diaphragm in response to stresses in the tissue caused by vessel pressure. The relative volume distribution of the fluid throughout the container can then be determined as it is caused by the deflection of the diaphragm. Third, additional fluid is supplied to the container until the relative volumes within each compartment are unchanged by arterial pulsations. Under these conditions, the diaphragm is undeformed relative to a starting, rest position. This starting position may be flat or any deflected shape that conforms to the wrist or other body part against which the diaphragm is placed. The pressure waveform within the vessel can then be determined using the pressure within the container when the diaphragm is in the rest position.

These and other features and objects of this invention will become apparent to one skilled in the art from the following detailed description and the accompanying drawings illustrating features of this invention by way of example.

BRIEF DESCRIPTION OF THE DRAWINGS

FIG. 1 is a perspective diagrammatic view of the tonometer of the present invention as applied to a patient's arm.

FIG. 2 is a partial cross-sectional view of the tonometer of FIG. 1.

FIG. 3 is a bottom view taken substantially along lines 3—3 of FIG. 2.

FIGS. 4A and 4B are diagrammatic illustrations of the interaction between a flexible diaphragm, a blood vessel and the tissue surrounding the blood vessel.

FIG. 14 is an exaggerated diagrammatic illustration of the tonometer of FIG. 10 with the flexible diaphragm moderately deflected.

DETAILED DESCRIPTION OF THE PREFERRED EMBODIMENTS

Figure 5:
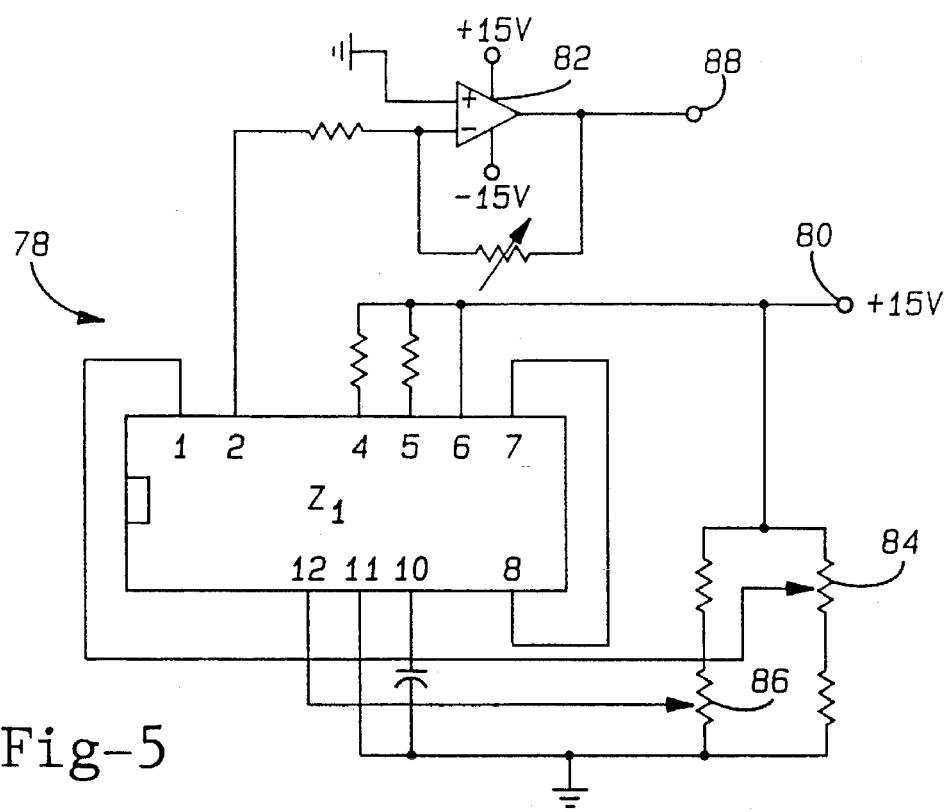
FIG. 5 is a schematic diagram of a current generator.

FIG. 1 shows a tonometry assembly 10 as applied to a patient's arm 12 to measure the pressure waveform within artery 13 in accordance with the present invention. Tonometer 14 is coupled with pressure transducer 16 which is shown in block diagram form. Signal processing means 18 is properly coupled to tonometer 14 and pressure transducer 16. Catheter 20 is provided to allow communication of fluid 23 between tonometer 14 and reservoir 22. Catheter 20 includes a two-way valve 24 for selectively controlling the amount of flow of fluid in either direction. Fluid 23 is preferably a saline solution because of its electrically conductive properties. Fluid 23 could also include other noncompressible solutions or gels or gas mixtures. Fluid 23 need not be electrically conductive. Alternatively, fluid 23 includes media that are conductive to microwave, ultrasound or optical signals, for example.

FIG. 2 shows, in cross-sectional view, the details of tonometer 14. Housing 30 forms sidewalls 31 and back wall 32 that define container 29 that contains fluid 23. Diaphragm 33 is stretched across the opening in housing 30 defined by sidewalls 31. Diaphragm 33 effectively seals off container 29 thereby maintaining fluid 23 within container 29.

As further detailed in FIG. 3, diaphragm 33 is maintained against housing 30 by a ring 34 which covers a portion of the outer periphery of diaphragm 33 and gasket 36. Gasket 36 and diaphragm 33 can be maintained in place by screws or fasteners 38 that are appropriately received in housing 30.

FIG. 2 also shows volume electrodes 40 which are preferably equally spaced across back wall 32 opposite diaphragm 33. Volume electrodes 40 effectively divide the container 29 into equal adjacent volume compartments. Current electrodes 42 are used to pass a current through noncompressible fluid 23 to determine the relative volume distribution within container 29 as caused by deflections in diaphragm 33. Electrodes 40 and 42 can be fashioned of stainless steel, for example. FIG. 3 also shows a fluid inlet 44 adapted to be connected to catheter 20 for supplying fluid 23 to container 29. Air outlet 46 is provided to ensure that container 29 is filled with fluid and that any unwanted air bubbles within fluid 23 can be released.

FIGS. 4A and 4B schematically represent container 29 divided into three volume compartments by volume electrodes 40. Three volume compartments are labeled $V_a$, $V_b$ and $V_c$. It is important to note that volume compartments $V_a$, $V_b$ and $V_c$ have no actual physical separation between them. Therefore, fluid 23 freely moves through and between the various volume compartments as required by any deflections in diaphragm 33. This relative communication between volume compartments provides the advantage of requiring monitoring of diaphragm deflection in only two or three regions corresponding to two or three volume compartments. This effectively eliminates the need for high resolution sensor technology as needed in previous tonometer designs. FIG. 4A shows diaphragm 33 deflected due to the pressure within artery 13 when diaphragm 33 is pressed against the tissue layer 56.

Tonometer 14 is placed against a patient's skin such that diaphragm 33 contacts tissue 56 near artery 13. Diaphragm 33 is effectively an extension of the tissue it contacts because it is capable of conforming to the contour of the wrist (or other body part). A preselected volume of noncompressible fluid 23 is contained within container 29 such that a pressure within container 29 permits diaphragm 33 to be deflected by arterial pressures within artery 13. Such a condition is illustrated diagrammatically in FIG. 4A. In FIG. 4A, the arterial pressure exceeds the pressure within the tonometer container 29 and the volume of the artery 13 effectively expands into volume compartment $V_b$. Volume compartments $V_a$ and $V_c$ responsively have increased volumes because of the expansion of the artery into volume compartment $V_b$. This occurs because the noncompressible fluid must be redistributed within container 29 because it is noncompressible and maintained at a fixed volume. A noncompressible fluid 23 is used in the illustrated embodiment for simplicity and because it is presently preferred, however, it is to be understood that gels or compressible gases are acceptable substitutes in accordance with this invention.

To establish a condition wherein flexible diaphragm 33 is maintained in a flat, rest position, the total volume within tonometer container 29 is increased as illustrated in FIG. 4B. The pressure within container 29 responsively increases and therefore, artery 13 flattens or applanates. Under the condition illustrated in FIG. 4B, the volume in each compartment is equal. Diaphragm 33 is essentially flat and tonometric calibration is achieved because the pressure within the tonometer is equal to the arterial pressure. Therefore, maintaining the volume compartments at an equal volume accomplishes one type of calibrated applanation tonometry with a flexible diaphragm. Alternative and more preferred methods of achieving calibrated tonometry will be discussed in greater detail below.

In one embodiment, controlling syringe 22 consistently and continuously maintains the amount of fluid 23 introduced into container 29 such that the relative volumes of each volume compartment are equal. This can be accomplished, for example, by coupling conventional sensor devices to tonometer 14 that interpret the volume information from the volume compartments and provide actuation signals to an electromechanical actuation means for adjusting the amount of fluid introduced by syringe 22. Alternatively, syringe 22 or any similar fluid reservoir could be monitored and adjusted by a person interpreting the signals from a proper sensing device. Solenoid activated or pneumatic means for adjusting the amount of fluid introduced by a reservoir 22 are acceptable and considered within the scope of this invention. Additional fluid can be added to or removed from container 29 according to the pressure within the artery such that the volume compartments have equal volumes. In the embodiment being presently described, the tonometer pressure is equal to arterial pressure whenever the compartment volumes are fixed and equal relative to each other.

In this manner, arterial tonometry is achieved with a lower resolution sensing array than the resolution required in previous tonometer devices. The feedback control algorithm associated with this invention employs volume compartment measurement signals to enable a volume correction device to maintain calibrated tonometry by continuously adjusting the container volume. The feedback system operates instantaneously and, therefore, produces a continuous variation in container pressure that tracks the vessel pressure.

CALIBRATION METHODOLOGY

This invention includes methodology for calibrating the tonometer including the flexible diaphragm 33. Calibration techniques are necessary because of the nature of the flexible diaphragm 33. The flexible diaphragm adapts itself to the contours of the body including the bones, tendons, and artery, for example. A device designed in accordance with this invention provides the advantage of giving superior comfort to a patient and more accurate signal transfer concomitantly to reducing the sensitivity of the tonometer to the position of the tonometer relative to the patient's body. Proper calibration includes determining when the volume of fluid 23 contained in container 29 has been adjusted to cause flexible diaphragm 33 to properly applanate the underlying vessel such that the pressure of the fluid in container 29 accurately represents the instantaneous pressure of the blood flowing through the vessel.

Adjusting the total volume within container 29 until all three volume compartments, $V_a$, $V_b$ and $V_c$ are equal provides a practical criteria for achieving a calibration condition for some tissue geometries. However, there are limitations to a calibration condition including the flat diaphragm because it may present discomfort to the patient or inaccurate results depending on the specific anatomy of the site where the tonometer is applied to the patient's body.

According to one method associated with this invention, diaphragm 33 is maintained in a flat position as discussed and generally illustrated in relation to FIGS. 4A and 4B. Volume feedback is used to prevent surface deflections along diaphragm 33 in order to achieve calibrated tonometry. Volume controlling circuitry and fluid reservoir 22 are coupled through an external catheter 20 to the tonometer volume compartments $V_a$, $V_b$ and $V_c$. The subsystem of flow electronics and the fluid reservoir shall be referred to generically as the volume control device. The volume control device can be used to adjust the volume within container 29 based upon the relative change in each compartment volume. An error signal can be determined by adding the pulse volumes. The error signal, therefore, represents a change in the flatness of the surface of diaphragm 33. As the error signal increases or decreases, the volume control device will cause additional fluid 23 to be added or removed from container 29 in order to adjust the tonometer fluid volume such that the error signal is maintained at its minimum, thereby keeping the flexible diaphragm 33 effectively rigid and flat.

Maintaining a flat surface along diaphragm 33 preferably is performed while concurrently maintaining the contact surface much stiffer than the artery and tissue system. It is known that tissue compliance is at a maximum value at a specific applanation pressure. Relative to the tissue, the tonometer will be at its maximum stiffness at the level of pressure where the tissue compliance is a maximum. Similarly, at this point the error signal will be smallest, indicating the best relative feedback control conditions. It is preferable to regulate the feedback error signal along two time frames. The feedback error signal should be regulated during each pulse and over several pulses. Therefore, tonometer calibration can be achieved by applying dynamic feedback in a slow or average feedback that attempts to minimize any dynamic feedback error.

In the presently preferred embodiment, a more general criteria is used to provide an automatable means of determining when calibrated conditions are established for tonometer 14. A more general criteria allows for differences in the relative volumes of the volume compartments $V_a$, $V_b$ and $V_c$ and therefore provides calibration information while the flexible diaphragm 33 is in a deformed or deflected position. In general, relative changes in each volume compartment are monitored as the total volume within container 29 is varied. When the relative changes between the individual volume compartments due to arterial pressure or pulsations are minimized, calibrated tonometry is achieved.

Referring now to FIGS. 10–14, the preferred methodology of calibrating tonometer 14 associated with this invention will be described. It is necessary to develop a model of tissue and vessel compliance in order to demonstrate the preferred methodology associated with this invention. The model for tissue and vessel compliance included herein is a very simplified model for purposes of enablement. It may be desirable to develop a more elegant, analytical model for vessel wall compliance for a more rigorous analysis depending on the level of accuracy required. The model used herein shall be referred to as the force-displacement analog lumped model.

Figure 10:
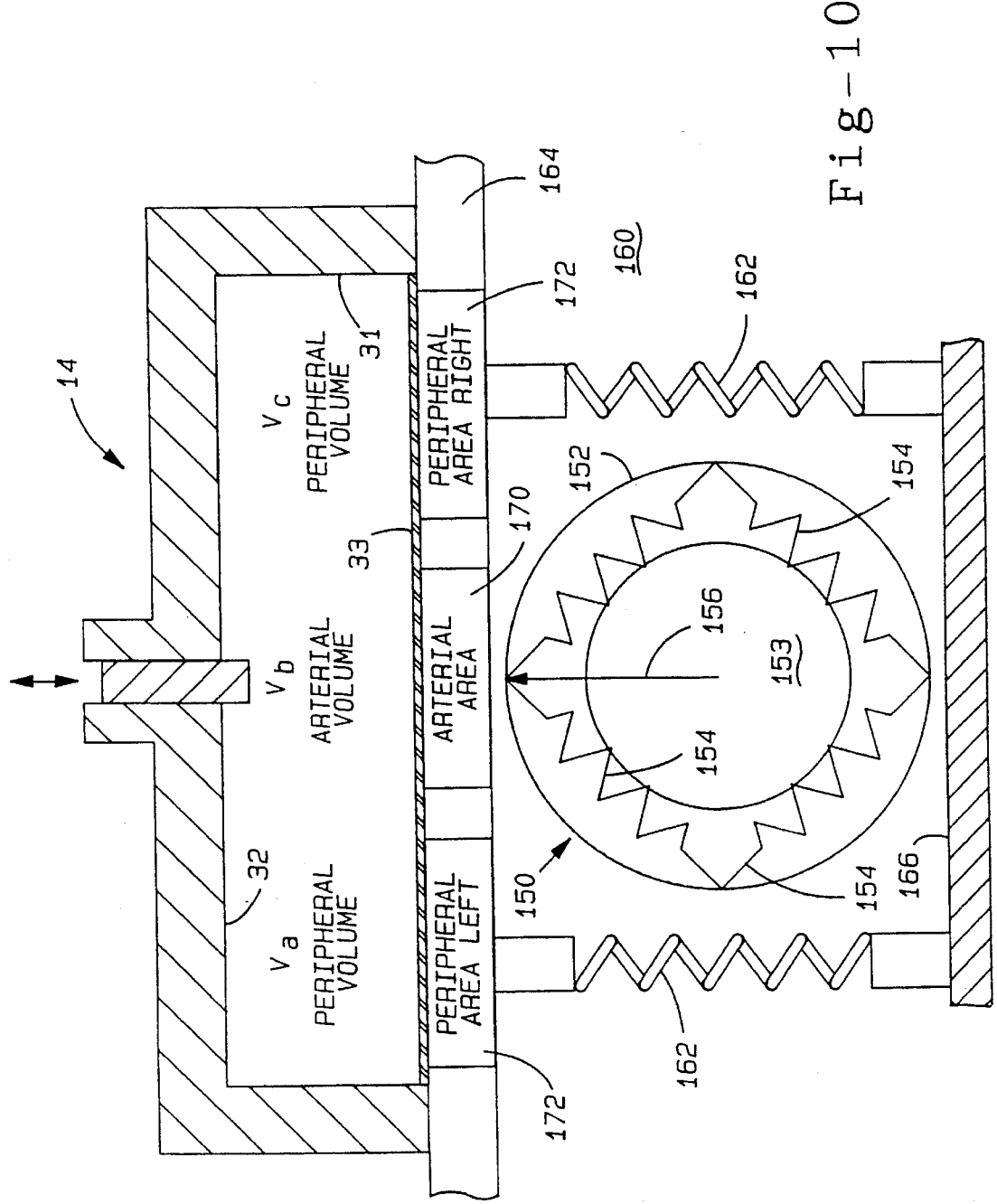
FIG. 10 is a partial sectional diagrammatic illustration of a tonometer designed in accordance with this invention placed against human tissue adjacent a blood vessel.

FIG. 10 diagrammatically illustrates the force-displacement analog lumped model of how the various forces involved in achieving calibrated tonometry interact. FIG. 10 shows artery 150 composed of arterial wall 152. The blood flows through artery 150 within the interior circle 153. Arterial wall 152 is shown with springs 154 having a spring constant $K_{wall}$. Springs 154 represent the forces introduced into the overall system by arterial wall 152. Arrow 156 shows the direction of the force of the blood flow through artery 150 as it would be interpreted by tonometer 14. The tissue surrounding artery 150 is shown at 160 and includes tissue springs 162. Springs 162 have a constant $K_{peripheral}$ which represents the forces imposed or introduced by the tissue surrounding artery 150. Surrounding tissue 160 is bordered by the skin layer 164, artery 150 and adjacent portions of bone 166.

Skin layer 164 is shown diagrammatically divided into three particular areas. Arterial area 170 corresponds to that portion of the skin layer 164 which lies adjacent artery 150. Peripheral areas 172 correspond to those portions of skin layer 164 that communicate with flexible diaphragm 33 on each side of arterial area 170. In the illustrated model, peripheral areas 172 and arterial area 170 are essentially contiguous with volume compartments $V_a$, $V_b$ and $V_c$, respectively.

Figure 11:
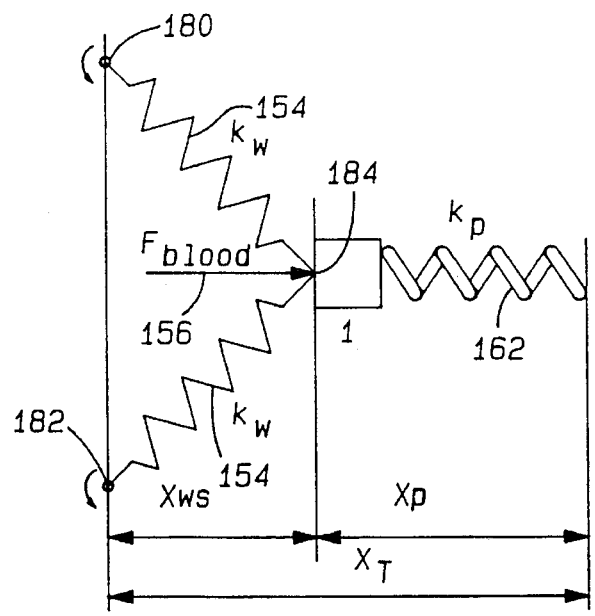
FIG. 11 is a diagrammatic model representation of the forces interacting within a blood vessel and the surrounding tissue.

FIG. 11 shows a reduced, selected portion of the system of FIG. 10 for purposes of simplification and illustration. Springs 154 and 162 are used because the force-displacement analog lumped model includes an analog of volume to displacement and pressure to force. In FIG. 11, arterial wall 152 is represented by the diagonal springs 154. Springs 154 rotate about fixed points 180 and 182, respectively. Springs 154 effectively pivot relative to each other at pivot point 184. Pivot point 184 also represents the point at which the force imposed by the blood flowing through vessel 150 is directed toward tonometer 14 and, more specifically, flexible diaphragm 33 as is indicated by force arrow 156. In FIG. 11, the peripheral or surrounding tissue 160 is represented by a single spring 162. The volume of container 29 is represented in FIG. 11 by the total displacement of the spring combination labeled $X_t$. The forces are created at the junction of the arterial wall 152 in the peripheral tissue 160; these forces are analogous to the fluid pressure within container 29. The total displacement $X_t$ corresponds to the total volume within container 29, therefore $X_t$ is varied as the total volume of fluid 23 is varied. The sum of forces acting at point 184 must be zero; this establishes the value of $X_w$ and $X_p$ which correspond to the central and side volume compartment volumes, respectively. It is important to note that, for simplification of this model, volumes have been converted to displacements. The springs 162 representing the peripheral tissue 160 and springs 154 representing the arterial wall 152 are illustrated in a series combination. A series combination is reasonable because of the transfer of forces through the fluid 23 within container 29.

Figure 12A:
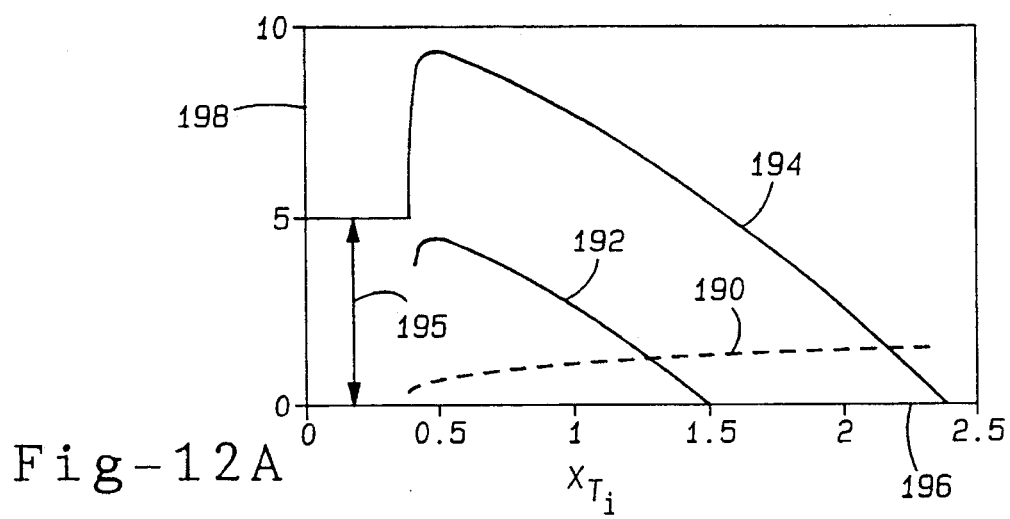
FIGS. 12A and 12B are plots of the arterial and tissue volumes and analogous forces diagrammatically illustrated in FIGS. 10 and 11.
Figure 12B:
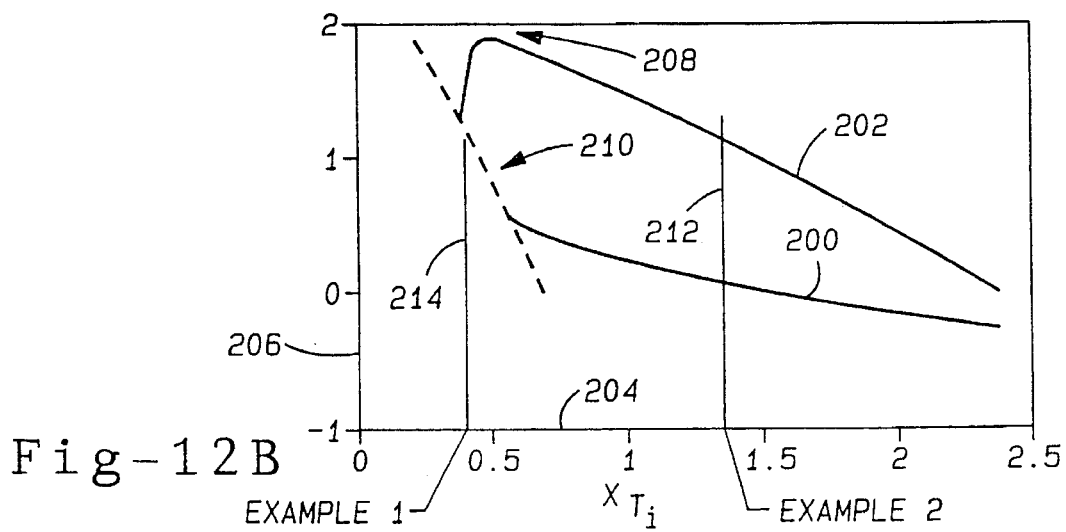

FIGS. 12A and 12B show selected plots of the various forces and volumes relevant to the force-displacement analog lumped model. FIG. 12A includes a plot of the linear displacement of the springs 154 which is shown as line 190 which corresponds to the linear displacement $X_w$. Plot 192 represents a plot of the force introduced by the arterial wall 152. Line 194 is a plot of the force introduced by the combination of the blood pressure within artery 150 and the force introduced by arterial wall 152. The force introduced by the blood pressure alone is indicated by arrow 195. Plots 190 through 195 are shown relative to a scale made up of a horizontal axis 196 representing, in conventional units, the total displacement $X_t$ and a vertical axis 198 showing increasing force in conventional force units.

FIG. 12B includes plot 200 showing the arterial volume which is the fluid volume within container 29 corresponding to the volume compartment or compartments corresponding to the portion of flexible diaphragm 33 that lies directly above or adjacent artery 150. Plot 202 represents the peripheral volume which corresponds to the fluid volume within container 29 in the volume compartments corresponding to the portions of flexible diaphragm 33 that lie adjacent peripheral areas 172 in skin layer 164 as illustrated in FIG. 10, for example. Plots 200 and 202 are shown relative to a scale which is defined by a horizontal axis 204 showing the total displacement $X_t$ as illustrated in FIG. 11 and the vertical axis 206 which shows an increasing volume in conventional volume units.

Tonometer calibration includes finding the optimum total container volume for accurate waveform measurement and analysis. The total volume within container 29 is varied until the optimum, calibrated conditions are achieved. The changes that result in arterial and peripheral volumes within container 29, and the analogous forces introduced by tissue 160 and artery 150 that occur because of the variation of the volume of fluid within container 29 are illustrated by the various plots in FIGS. 12A and 12B. It is important to note, in FIGS. 12A and 12B that increasing the volume within container 29 corresponds to a decreasing value of the displacement variable $X_t$. As the volume in container 29 is increased, the pressure (or, according to the model, $F_{wall}$ and $F_{peripheral}$ tissue) increases up to a maximum value which is indicated approximately at the point 208. As indicated in the plot in FIG. 12A, the pressure then suddenly decreases as the wall 152 collapses, losing its ability to create or introduce a force. In the model diagrammatically illustrated in FIG. 11, this condition corresponds to the two springs 154 rotating into an essentially vertical alignment relative to each other. At this point they no longer produce any force in the horizontal direction (according to the drawing). Therefore, the only force remaining is that of the blood pressing outward as indicated by force arrow 156. A further increase of the total volume within container 29 should not affect the mean blood pressure within artery 150.

As illustrated in FIG. 12B, the change in peripheral and arterial volumes is concurrent with the change of total volume and therefore, the fluid pressure within container 29. As the total volume within container 29 increases, the arterial volume progressively increases in a linear fashion until arterial wall 152 collapses. At this point the arterial volume increases rapidly, establishing a new and much steeper slope indicated at 210, with respect to the increase in total volume. Similarly, the peripheral volume increases linearly with the increasing volume of container 29. As the volume within container 29 is transferred to the arterial region during the collapse of arterial wall 152, the peripheral volumes suddenly decrease, creating a reversal to a negative going slope as illustrated in plot 202. These two significant changes in pressure and volume compared to the total volume within container 29 provide the information necessary to achieve a calibrated tonometry condition which allows for automatic control of the volume within container 29 to thereby provide continuously calibrated operation of tonometer 14.

Figure 13:
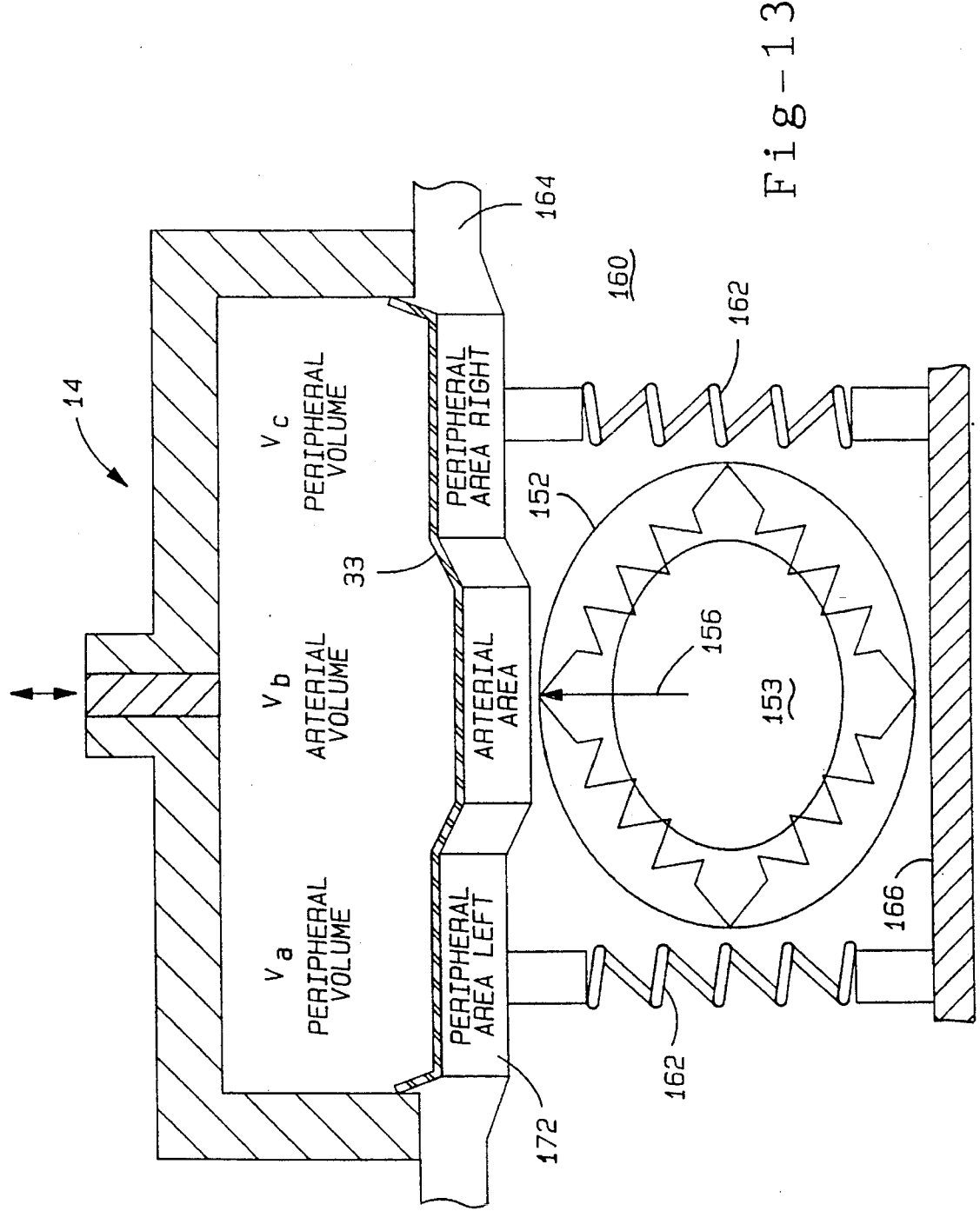
FIG. 13 is an exaggerated diagrammatic illustration of the tonometer of FIG. 10 with the flexible diaphragm slightly deflected.

Assuming FIG. 10 illustrates an initial position of flexible diaphragm 33 as applied to skin layer 164, FIGS. 13 and 14 illustrate, diagrammatically, the effects upon flexible diaphragm 33, artery 150, surrounding tissue 160 and skin layer 164 that an increased volume within container 29 causes. FIG. 13 diagrammatically illustrates, in an exaggerated form, the response of this system when the total volume within container 29 is increased a small amount. The arterial and peripheral wall volumes within container 29 are both increased. However, the arterial volume increases at a faster rate than the peripheral volumes. For simplicity, the arterial volume corresponds to the volume within volume compartment $V_b$ and the peripheral volumes would correspond to the volumes within volume compartments $V_a$ and $V_c$, respectively. The condition illustrated in FIG. 13 corresponds to the point in the graph of FIG. 12B indicated at 212.

FIG. 14 diagrammatically illustrates, in exaggerated form, the response of the system when the total volume within container 29 has been increased a relatively large amount. In FIG. 14, the arterial wall 152 has been compressed and the peripheral volume (i.e., the volumes within volume compartments $V_a$ and $V_c$) has decreased. The conditions illustrated in FIG. 14 correspond to the point in FIG. 12B illustrated at 214. Accordingly, the optimum conditions for calibrated tonometry correspond to a volume within the container somewhere between the relative volumes illustrated in FIGS. 13 and 14, respectively.

Keeping a calibrated operating condition for tonometer 14 can be described generally as follows, based upon the model just described and illustrated. First, the volume within container 29 is preferably adjusted until the sensor pressure registers approximately at a zero value. This value pressure point can be considered the initial operating point or that condition under which the flexible diaphragm 33 is maintained in a rest position. Next, the volume within container 29 is progressively increased while the slope of the curves of the arterial volume and the peripheral volume within container 29 versus the total volume within container 29 are concomitantly monitored. The volume within container 29 is increased until the volumes within volume compartments $V_a$ and $V_c$, i.e. the peripheral volume, reach a maximum and then decrease a predetermined percent below the maximum value. Concurrently, the slope of the arterial volume versus total volume curve is monitored to find an increase in that slope. When both conditions are met, one boundary of the range of container volumes 29 that provide calibrated tonometer operation is found. Increasing the total volume within container 29 by a relatively small additional amount would bring the operating point of tonometer 14 somewhere within region 216 as illustrated in FIG. 12A. At this point, the total volume in container 29 is held constant and the pressure within fluid 23 is monitored and considered the estimate of the true arterial blood pressure within artery 150. This operating point is called the static equilibrium operating point. Under certain conditions it may be necessary, over time, to reduce the volume and reestablish the calibrated operating point of tonometer 14 if the patient repositions the sensor such that diaphragm 33 is in a different site than it previously was located.

Therefore, the difference between the calibrated condition wherein the diaphragm is maintained in an essentially flat condition and the calibrated condition, which is presently preferred in connection with this invention, lies in how the volumes within the various volume compartments within container 29 are monitored. In the first instance, wherein the diaphragm is maintained in a relatively flat position, the volumes within each volume container compartment or transducer are preferably maintained equal to each other. In the presently preferred approach, calibration is achieved by monitoring the behavior of the changes in the volume and pressure as described above until the optimum operating conditions are met and calibration is achieved. It is important that the relative changes between the respective volume compartments as caused by vessel pulsations be kept at a minimum. Continuous tonometry and calibration can then be maintained by maintaining a volume of fluid 23 within container 29 such that the individual volumes of each volume compartment remain relatively unchanged by arterial pulsations. In other words, a representative set of measurements for arterial and peripheral volumes (i.e the volumes within the various volume compartments) are chosen and then the total volume within container 29 Is dynamically adjusted to hold the respective volume compartment values in the same ratio during each heartbeat within the patient. Therefore, calibrated tonometry is achieved and maintained providing the ability to continuously monitor the blood pressure waveform within a vessel such as artery 150 or 13.

VOLUME MEASUREMENT

The inventive flexible diaphragm tonometer includes an array of volume transducers as described above. Volume can be detected by a variety of techniques conventionally referred to as plethysmography. One technique that is preferred in association with the present invention is conventionally known as impedance plethysmography. Impedance plethysmography is preferred because the volume compartments are filled with fluid. The noncompressible fluid used with one embodiment of this invention is preferably saline because saline has conductive properties. The presence of saline allows the resistance of each compartment to be measured and related to each compartment volume. Other conductive solutions could be used.

Assuming that each compartment is rectangular in shape, resistance is given by the equation:

$$R=rL/A \qquad (1)$$

where r=the resistivity of saline;

L=the compartment length; and

A=the cross-sectional area of the volume compartment.

Since compartment volume is equal to the length of the compartment multiplied by the cross sectional area of the compartment, it follows that:

$$R=rL^2/V \qquad (2)$$

where V=compartment volume. Therefore, total container volume can be determined by measuring the resistance of each volume compartment. This can be accomplished by injecting a current, I, through fluid 23 such that a voltage, v, is imparted across each pair of electrodes 40 that can be used to measure the volume of the compartment according to the following equation:

$$v=IR=IrL^2/V \qquad (3).$$

Current electrodes 42 can be used to inject such a current through the length of tonometer container 29.

For example, current electrodes 42, can be supplied with a 10 kilohertz sine wave at approximately 1 milliamp of current. The relatively high frequency is preferred in order to minimize the electrode impedance and prevent electrode polarization. Such an electrode current can be generated by the circuitry illustrated schematically in FIG. 5.

FIG. 5 illustrates a current generator 78 including component $Z_1$, power supply 80 and operational amplifier 82. Component $Z_1$ is a commercially available chip known as an Intersil ICL8038. Component $Z_1$ is used to generate a sine wave output. Operational amplifier 82 is connected to pin 2 of $Z_1$ to serve as an output buffer. Pins 1 and 12 are coupled to power supply 80 through variable resistors 84 and 86, respectively. Variable resistors 84 and 86 serve as means for adjusting the frequency and amplitude of the output of sine wave generator $Z_1$. The output signal at 88 is appropriately coupled to current electrode 42 (FIG. 2). The current generator 78 is part of signal processing means 18.

Figure 6:
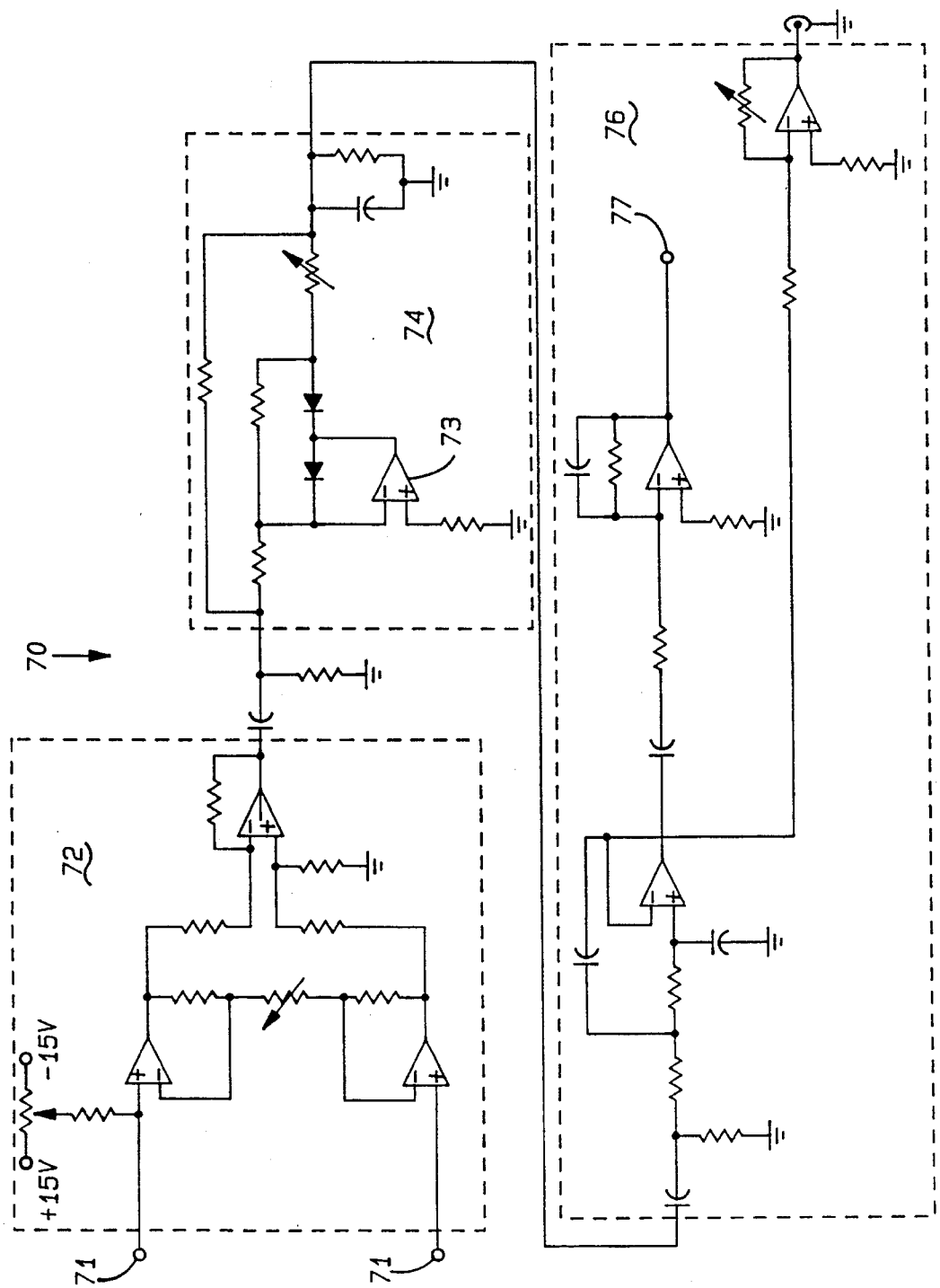
FIG. 6 is a schematic diagram of a volume electrode signal processing circuit.

The sine wave used as a current supply to tonometer 14 should be demodulated and filtered for arterial pressure frequencies. Each pair of volume electrodes 40 is preferably coupled to the same signal processing circuit; an example of which is illustrated in FIG. 6. FIG. 6 illustrates a differential input amplifier 70, constructed of operational amplifiers, that serves as a means for finding the voltage across a pair of volume electrodes 40 and providing a high impedance to minimize electrode impedance effects. A pair of volume electrodes 40 are respectively connected to inputs 71. The electrode voltage is preferably amplified and high pass filtered by filter 72 before measurements are derived in order to remove any constant off-set voltage. Demodulation of the sine wave voltage can be accomplished by the third stage operational amplifier 73 which is part of precision full wave rectifier and averaging filter 74. Frequencies are preferably limited to less than 30 Hertz. The voltage output of the demodulator means 74 is related to the volume between the selected electrode pair. An amplifier stage 76 serves as a means for providing calibration adjustment and output buffering. The pulse component is filtered using a bandpass filter preferably between 0.5 and 30 Hertz. The pulsatile volume is also amplified and calibrated at this stage. Therefore, the volume determining electronics 70, properly coupled with a pair of volume electrodes 40, outputs a voltage at 77 calibrated to equal the compartment volume between the corresponding electrode pair and any pulsatile change in that volume.

Figure 7:
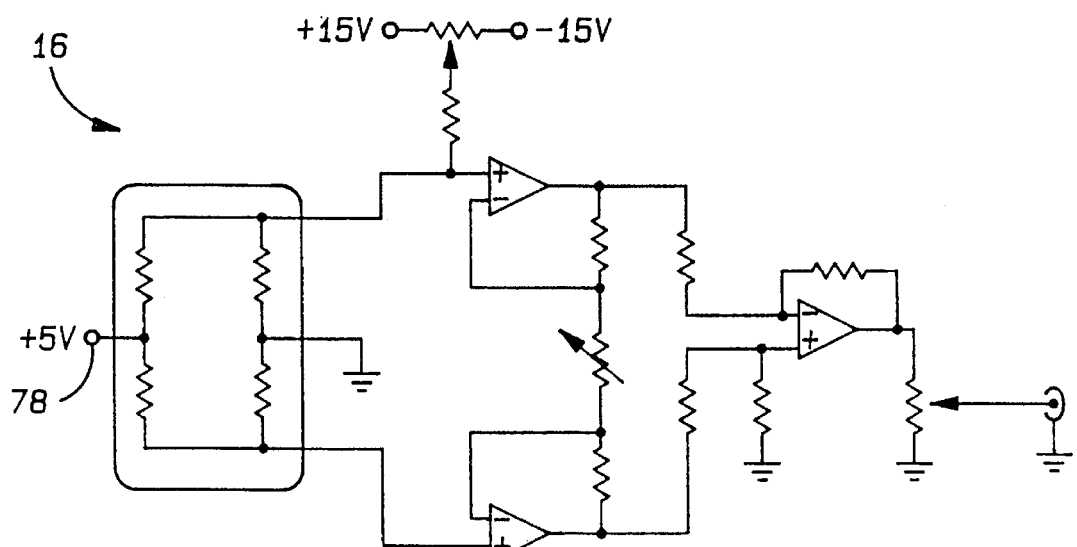
FIG. 7 is a schematic diagram of a pressure transducer including a strain gauge bridge amplifier.

Pressure transducer 16 preferably includes electronics as illustrated in FIG. 7 including a strain gauge differential bridge amplifier. Transducer 16 is preferably supplied with a constant excitation DC voltage 78, zero offset and calibration controls. The strain gauge amplifier included in transducer 16 works similar to any conventional strain gauge amplifier; pressure within container 29 imparts a stress on transducer 16 such that a voltage signal is produced that is proportional to the container pressure. Pressure transducer 16 can be calibrated using a mercury manometer prior to appropriately connecting the transducer to the tonometer assembly 10. Transducer 16 can be coupled to catheter 20 or directly to container 29, for example. Each volume compartment can be calibrated by injecting a known volume of fluid into container 29 using syringe 22. A fraction of the volume between a given pair of electrodes or the fraction of the volume within a volume compartment can be determined from the interelectrode distance as a fraction of the total length of tonometer container 29.

All volume compartments are preferably calibrated prior to applying the flexible diaphragm to the skin and tissue adjacent or above the vessel of interest. For example, all volume compartments should be calibrated prior to placing tonometer 14 above the radial artery in the wrist of a patient. Tonometer 14 is preferably centered above the radial artery. Proper centering can be accomplished by first palpating for the vessel and then centering tonometer 14 over that point. Pulse volume output can be monitored from the center volume compartment defined by the center electrode pair. Minor repositioning of tonometer 14 can help to achieve an exact centering by repositioning tonometer 14 until the largest waveform is produced from the center electrode channel or volume compartment. Tonometer 14 can then be secured to the patient, for example, by wrapping a velcro strap around the device and the patient's wrist. The patient preferably should refrain from motion during waveform recording.

Several heartbeats of tonometer data can be monitored over time from the pulse volume recordings and each individual channel defined by the pair of electrodes can be monitored or graphed separately to show the relationship between and among them. A patient's diastolic, systolic and mean blood pressure can be determined. The pulse volume is referenced as a volume deviation from the mean compartment volume within each volume compartment. A constant average level of tonometer pressure can be determined. Because the volume compartments are in relative communication with each other, as arterial volume increases the compartment volumes adjacent the artery will decrease. This characteristic of tonometer 14 permits measurement of the pulse volume to be determined at any desired external applanation pressure. The average volume within container 29 can be obtained from the individual channel volume records.

MEASURING TISSUE AND ARTERY COMPLIANCE

Tonometer 14 also provides the ability to measure tissue compliance and arterial compliance. Tissue compliance can be obtained by determining the derivative of the volume curve that describes the volume within container 29. Tissue compliance exhibits a maximum near a patient's mean arterial pressure. This is expected because the vessel must collapse when the transmural pressure is less than zero and the tissue compliance is that of skin and an artery wall.

Arterial compliance can be obtained when the volume feedback control is disabled; allowing the diaphragm to be completely flexible. The change in container volume can be assumed to be the pulse volume. The change in pressure within container 29 is effectively a constant pulse pressure obtained from the systolic minus the diastolic pressure. It follows, by definition, that the arterial compliance is equal to the change in the volume divided by the change in the pressure. Experiments indicate that arterial compliance alters depending on the tonometer pressure. Arterial compliance maximizes at the value of mean arterial pressure. Experiments also indicate that compliance decreases with the tonometer pressure, therefore, verifying the classic physiological observation that the arterial wall stiffens with increasing internal pressure. Conversely, by applying external tonometer pressure, the vascular wall effectively has a reduced load allowing it to become more compliant.

The flexible diaphragm tonometer allows the artery to move freely so that volume pulsation can be measured and arterial compliance can be determined. This valuable hemodynamic information is an additional benefit and feature inherent in a tonometer designed in accordance with this invention. A flexible diaphragm tonometer provides a considerable improvement over compliance methods that rely on plethysmography of a limb or finger, since the inventive tonometer provides pressure data for a single artery rather than a volume of tissue. Moreover, the inventive flexible diaphragm tonometer is adaptable to monitoring the pressure waveform in a variety of blood vessels, including relatively small vessels.

WAVEFORM ANALYSIS

One question that arises while non-invasively measuring arterial pulse is whether the waveform is correct. This invention includes a method and apparatus for monitoring the quality of the pulse waveform. Experiments indicate that the waveform alters its shape depending on applanation pressure. Such results do not address whether the pressure calibration is correct, but whether the pulse signal is truly proportional to the pressure.

Assume, that a typical pulse sensor receives the arterial pulse through a skin and artery system. Such a system is predominantly nonlinear with a narrow linear range where tonometry functions as expected. Therefore, for a tonometer, a pulse signal is expectedly directly proportional to the arterial pressure. This phenomena can be described by the following equation:

$$S(t)=A+Bp(t) \qquad (4)$$

where p(t)=the arterial pulse; and
A,B=constants.

Assuming that the arterial pulse is a simple sine wave yields:

$$S(t)=A+B\sin(2\pi f) \qquad (5)$$

where f= the heart rate. If the pulse transducer is positioned improperly, then, it will likely be nonlinear such that:

$$S(t)=A+Bp(t)+Cp^2(t)+dp^3(t)+ \qquad (6).$$

Further, by assuming the simplest case of second order nonlinearity and a sine wave input, the system is described by the following equation:

$$S(t)=A+B\sin(2\pi f)+C\sin^2(2\pi f) \qquad (7)$$

and from trigonometry:

$$S(t)=A+B\sin(2\pi f)+C(1-\sin(2\pi f+\pi/2))/2 \qquad (8)$$

Therefore, simple second order nonlinearity adds a phase-shifted frequency component at double the original heart rate. As one analyzes the pressure pulse waveform, one finds that any frequency component will be doubled and added to the recorded pulse waveform. This will be referred to as harmonic pulse distortion.

Figure 8:
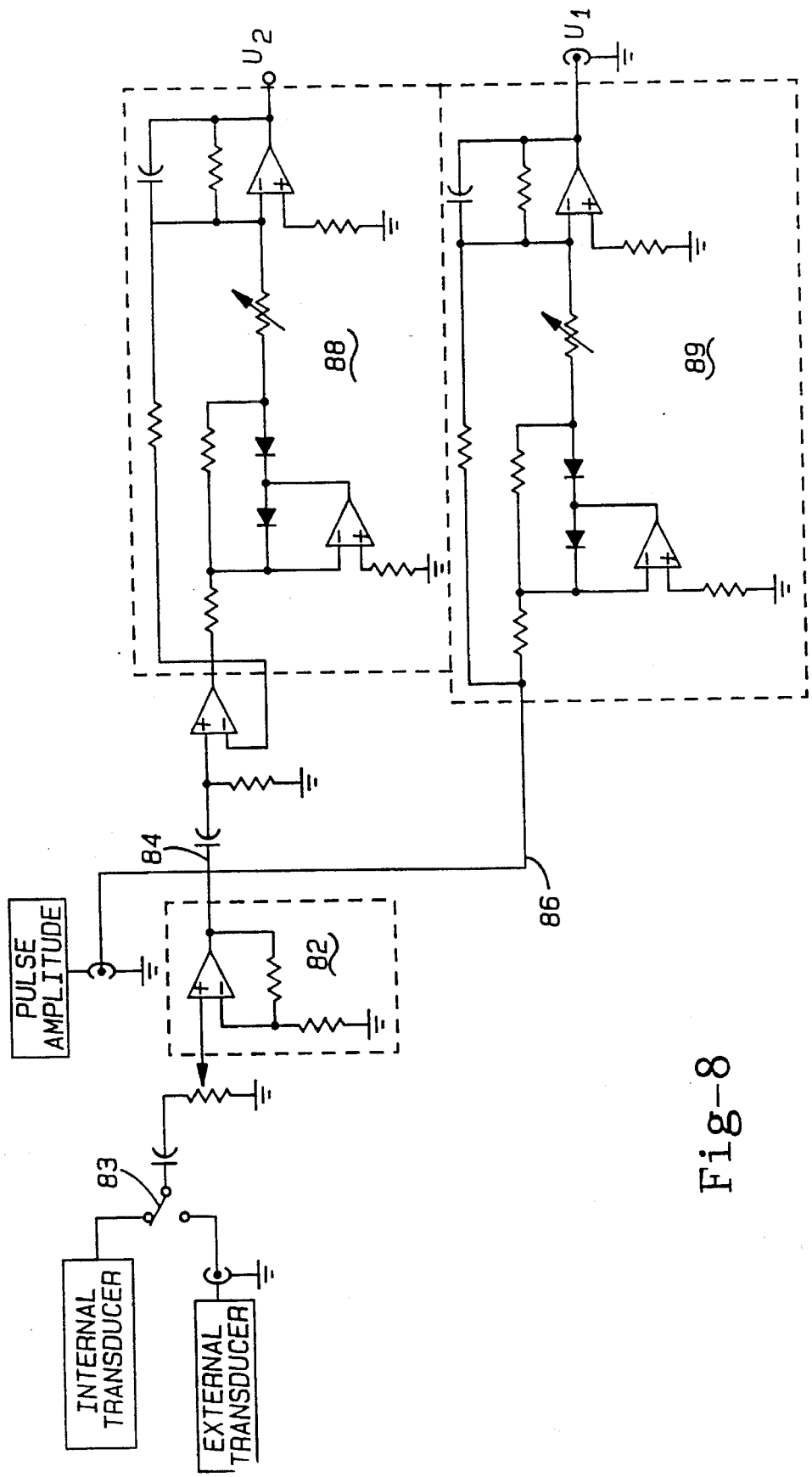
FIG. 8 is a schematic diagram of a pulse waveform analyzer.

Any electronic pulse waveform analyzer, such as that illustrated in FIG. 8, can be used to reduce harmonic pulse distortion of the arterial pulse recording. The electronic pulse waveform analyzer is used to identify the ratio of average high frequency pulse signals to average total pulse signals. This ratio can be monitored while adjusting the pulse transducer positioning in order to obtain a minimum, and thereby, minimal pulse harmonic distortion.

The circuit illustrated in FIG. 8 can serve as such a pulse waveform analyzer and functions generally as follows. First, the pulse signal is high-pass filtered by filter 82 to remove any offset voltage. Then, by actuating switch 83, the signal is high-pass filtered, by filter 82, again preferably at approximately 5 Hertz to obtain the high frequency portion of the pulse. In this manner, two channels of data are created; a total pulse channel 86 and a high frequency pulse channel 84. Each of these are passed through an absolute value amplifier and average 88, 89. The ratio of each average signal is then determined by an analog divider circuit. An example of such an analog divider circuit is illustrated schematically in FIG. 9.

Figure 9:
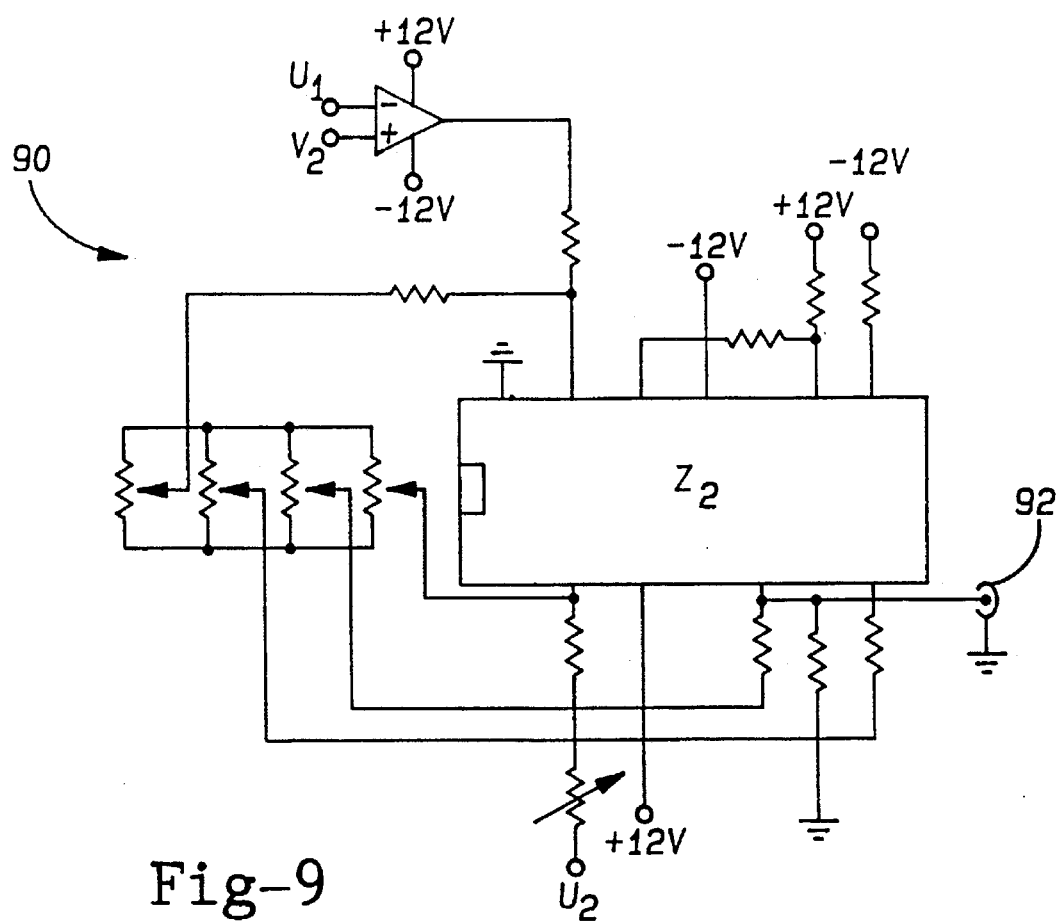
FIG. 9 is a schematic diagram of an analog signal divider.

The divider circuitry 90 of FIG. 9 functions as any conventional electronic signal divider. The illustrated embodiment includes component $Z_2$ which is preferably a commercially available chip designated as CA3091/D chip. Inputs at $U_1$ and $U_2$ are coupled to outputs $U_1$ and $U_2$ in FIG. 8 as described above. The output $V_0$ at 92 is equal to $U_2/U_1$. Therefore, the spectrum ratio obtained at output 92 is equal to the average of the absolute value of the high frequency pulse signal divided by the average of the absolute value of the pulse signal.

The output of pressure transducer 16 is appropriately coupled to the circuit of FIG. 8. When the tonometer 10 is centered correctly over the artery while applanation pressure is altered, the ratio of output versus the applanation pressure reveals that a minimum in the ratio can be obtained. This minimum indicates that too much or too little applanation resorts in distortion of the pulse and that there is one optimal position for the transducer. This optimal position provides a measure of the pulse waveform with the least amount of harmonic pulse distortion. Therefore, an electronic pulse waveform analyzer in accordance with this invention offers guidance in determining the correct position of the tonometer. Experiments indicate that often a broad minimum occurs, indicating that the tissue system does not have sufficient nonlinearity for an exact quality analysis. It is recognized that a good pulse waveform can be obtained in many positions. Moreover, it should be recognized that arterial frequency dependent properties are assumed to be independent of tonometer position. Current studies indicate that this relationship between tonometer position and arterial properties is approximately true. However, some positions may not provide properly calibrated tonometry. It is recognized, therefore, that such a pulse waveform analyzer provides a measure of waveform quality and may have the additional purpose of serving as a second check on proper or accurate positioning.

The advantages of a tonometer designed in accordance with this invention include the ability for true long term non-invasive pulse waveform monitoring. The inventive tonometer has the ability to obtain accurate beat-to-beat and long-term waveform data. A tonometer designed in accordance with this invention is easily adaptable to a variety of vessels within a patient. Small vessel size Is more easily accommodated by the inventive tonometer compared to conventional tonometry. The inventive tonometer has the further advantage of being more robust in reducing motion and positioning artifacts due to its inherently low resolution characteristics.

The preceding description is exemplary rather than limiting in nature. A preferred embodiment of this invention has been disclosed to enable one skilled in the art to practice this invention. Variations and modifications are possible without departing from the purview and spirit of this invention; the scope of which is limited only by the appended claims.

We claim:

1. A method of noninvasively monitoring the pressure waveform of a vessel, comprising the steps of:

(A) providing a container filled with a volume of fluid and having a flexible diaphragm forming one side of the container, the flexible diaphragm having a calibrated position;

(B) placing the flexible diaphragm against tissue generally covering the vessel such that the diaphragm effectively becomes an extension of the tissue whereby the diaphragm is deflected across a portion of the diaphragm in response to stresses in the tissue against which it is placed, the stresses being caused by vessel pressure;

(C) adjusting the volume of fluid within the container to return the diaphragm to the calibrated position from the deflected position; and (D) determining the pressure within the container when the diaphragm returns to said calibrated position, whereby the pressure waveform of a vessel is determined.

2. The method of claim 1, wherein step (A) further comprises the substep of dividing the container into a plurality of volume compartments that are in relative communication such that the fluid moves freely between the compartments.

3. The method of claim 2, wherein step (C) comprises the substeps of determining the fluid volume within each volume compartment and defining a condition wherein the diaphragm is not in the calibrated position as a condition wherein the respective fluid volumes within each volume compartment are changing relative to each other.

4. The method of claim 3, wherein step (C) is performed by the substeps of supplying additional fluid to the container when the diaphragm is not in the calibrated position until the respective volumes within the volume compartments are maintained relatively unchanged thereby returning the diaphragm to said calibrated position.

5. The method of claim 1, wherein step (A) further comprises the substep of providing a plurality of volume electrodes within the container to thereby divide the container into a plurality of volume compartments, each of said volume compartments defined by a pair of volume electrodes, respectively.

6. The method of claim 5, wherein step (A) further comprises the substeps of providing a pair of current electrodes within the container and injecting a current into the container through the fluid using the current electrodes.

7. The method of claim 6, wherein step (C) comprises the substep of determining a voltage across a selected volume compartment to thereby determine the fluid volume within the selected volume compartment.

8. The method of claim 7, wherein the step of determining the voltage further comprises the steps of:

detecting a modulated voltage signal across a pair of volume electrodes defining the volume compartment, the modulated voltage resulting from the modulated current injected into the container;

filtering the modulated voltage signal to thereby produce a filtered voltage signal; and demodulating the filtered modulated voltage signal to thereby produce a volume signal that is proportional to the fluid volume within the volume compartment.

9. The method of claim 6, wherein the step of injecting comprises the step of injecting a modulated current into the container through the fluid using the current electrodes.

10. A method of noninvasively monitoring the pressure waveform of a vessel, using a flexible diaphragm tonometer, comprising the steps of:

(A) placing a flexible diaphragm tonometer having a plurality of volume compartments adjacent tissue generally surrounding the vessel;

(B) monitoring the respective volume of each volume compartment and placing the tonometer in a calibrated condition; and (C) determining the pressure within the tonometer when the tonometer is in the calibrated condition, whereby the pressure waveform of the vessel is determined.

11. The method of claim 10, wherein step (B) comprises the further substeps of defining the calibrated condition as the condition wherein the respective volumes of the volume compartments remain in an essentially fixed ratio and maintaining the relative volumes in the essentially fixed ratio to thereby maintain the tonometer in the calibrated condition.

12. The method of claim 10, wherein step (B) comprises the substeps of:

(i) including an arterial compartment and a peripheral compartment among the plurality of volume compartments of the tonometer;

(ii) adjusting a total volume within the tonometer such that a preselected pressure is maintained within the tonometer;

(iii) increasing the total volume within the tonometer until a set of calibration conditions are satisfied; and (iv) maintaining the total volume within the tonometer constant at a volume slightly greater than the volume corresponding to the set of calibration conditions of substep (iii).

13. The method of claim 12, wherein substep (iii) comprises the further substeps of:

monitoring the volume within the arterial compartment relative to the total volume; and monitoring the volume within the peripheral compartment relative to the total volume.

14. The method of claim 12, wherein the set of calibration conditions are defined as the conditions wherein the volume within the peripheral compartment reaches a maximum value and subsequently decreases a predetermined amount, and the volume within the arterial compartment increases relatively slower than the total volume concurrently increases.

* * * * *